United States Patent [19]

Jacobs et al.

[11] Patent Number: 4,495,636
[45] Date of Patent: Jan. 22, 1985

[54] MULTICHANNEL RADIOGRAPHY EMPLOYING SCATTERED RADIATION

[75] Inventors: Alan M. Jacobs, Gainesville, Fla.; Edward S. Kenney, State College; Joseph J. McInerney, Hummelstown, both of Pa.

[73] Assignee: Research Corporation

[21] Appl. No.: 222,133

[22] Filed: Jan. 2, 1981

[51] Int. Cl.³ .......................................... G01N 23/20
[52] U.S. Cl. ......................................... 378/87; 378/91
[58] Field of Search ............................. 378/87, 6, 91

[56] References Cited

U.S. PATENT DOCUMENTS

| 2,079,900 | 5/1937 | Cohn | 250/34 |
| 3,718,817 | 2/1973 | Afanasjev et al. | 250/43.5 FL |
| 3,769,507 | 10/1973 | Kenney et al. | 250/52 |
| 3,792,269 | 2/1974 | Grienauer | 250/272 |
| 3,833,810 | 9/1974 | Elanov et al. | 250/373 |
| 3,868,506 | 2/1975 | Ogiso | 250/278 |
| 3,989,944 | 11/1976 | Birka et al. | 250/272 |
| 4,101,774 | 7/1978 | Elzinga et al. | 250/402 |
| 4,124,804 | 11/1978 | Mirell | 250/358 |
| 4,190,772 | 2/1980 | Dinwiddie et al. | 250/445 T |
| 4,195,227 | 3/1980 | Carman et al. | 250/505 |
| 4,204,123 | 5/1980 | Stoddart | 250/363 S |
| 4,209,700 | 6/1980 | Stoddart | 250/363 S |
| 4,229,651 | 10/1980 | Danos | 378/87 |

OTHER PUBLICATIONS

"Dynamic Radiography—a Technique Employing Scattered Radiation to Monitor Surface Motion," *Medical and Biological Engineering*, by Tilley et al., vol. 14, pp. 141-149, (Mar. 1976).

Primary Examiner—Craig E. Church
Attorney, Agent, or Firm—Scully, Scott, Murphy & Presser

[57] ABSTRACT

A diagnostic imaging system and process permits construction of an image of an area of an interfacial surface within the body of a subject, such as the heart-lung interface. The imaging system includes radiation source means for generating a shaped beam of penetrating radiation for illuminating the interfacial surface. Radiation scattered from tissue at the interface is detected by a plurality of directional radiation detectors which can be automatically positioned and oriented so that their fields of view intersect the beam of radiation and the interfacial surface.

20 Claims, 11 Drawing Figures

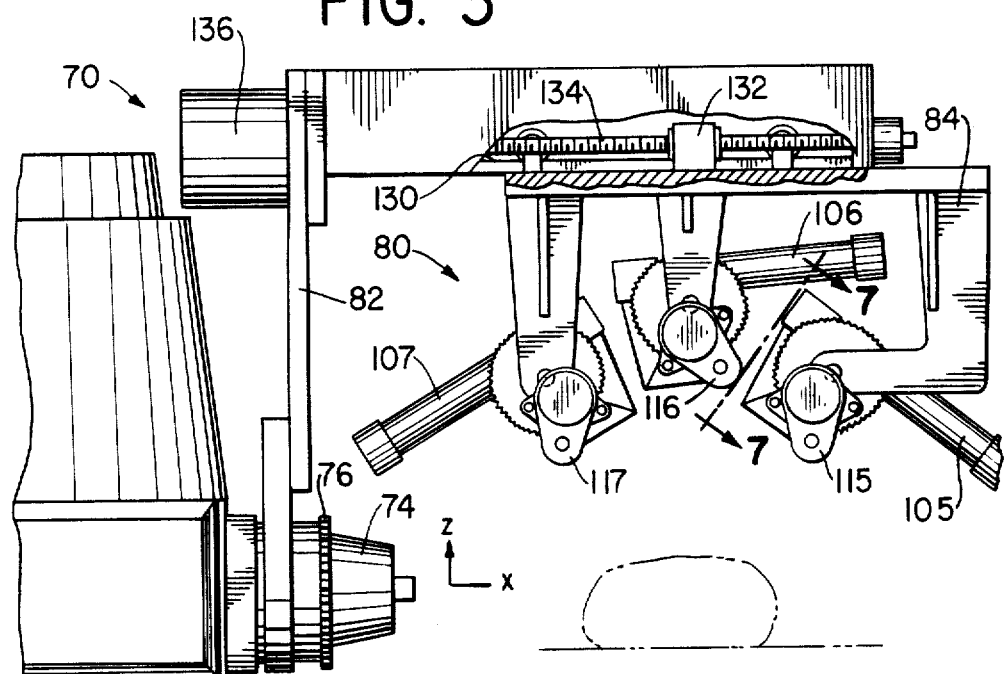
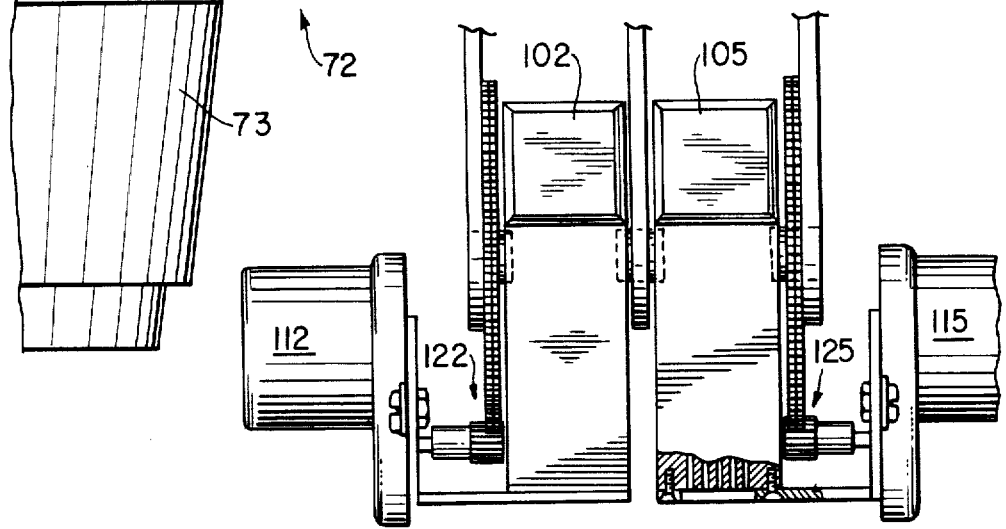

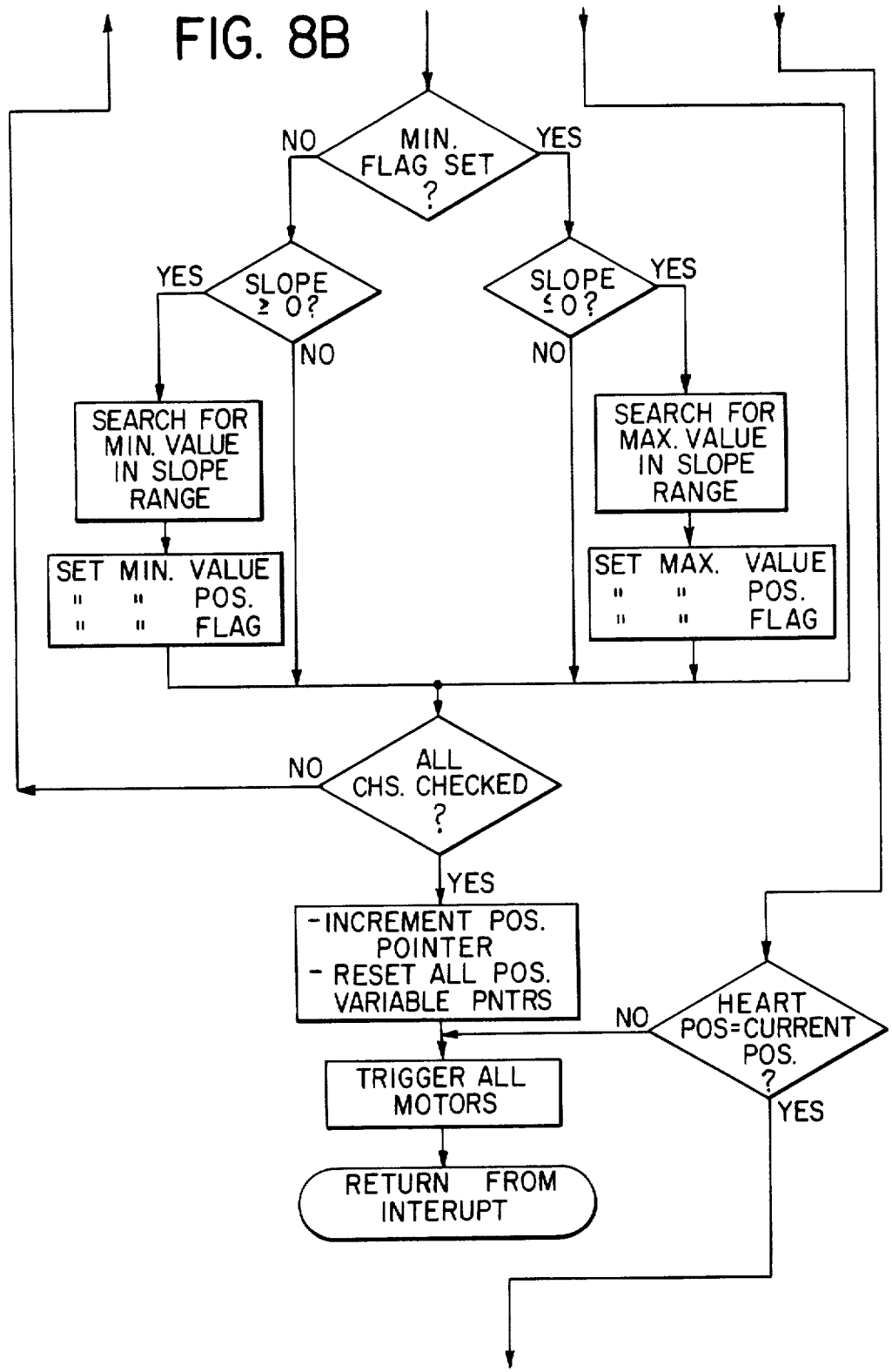

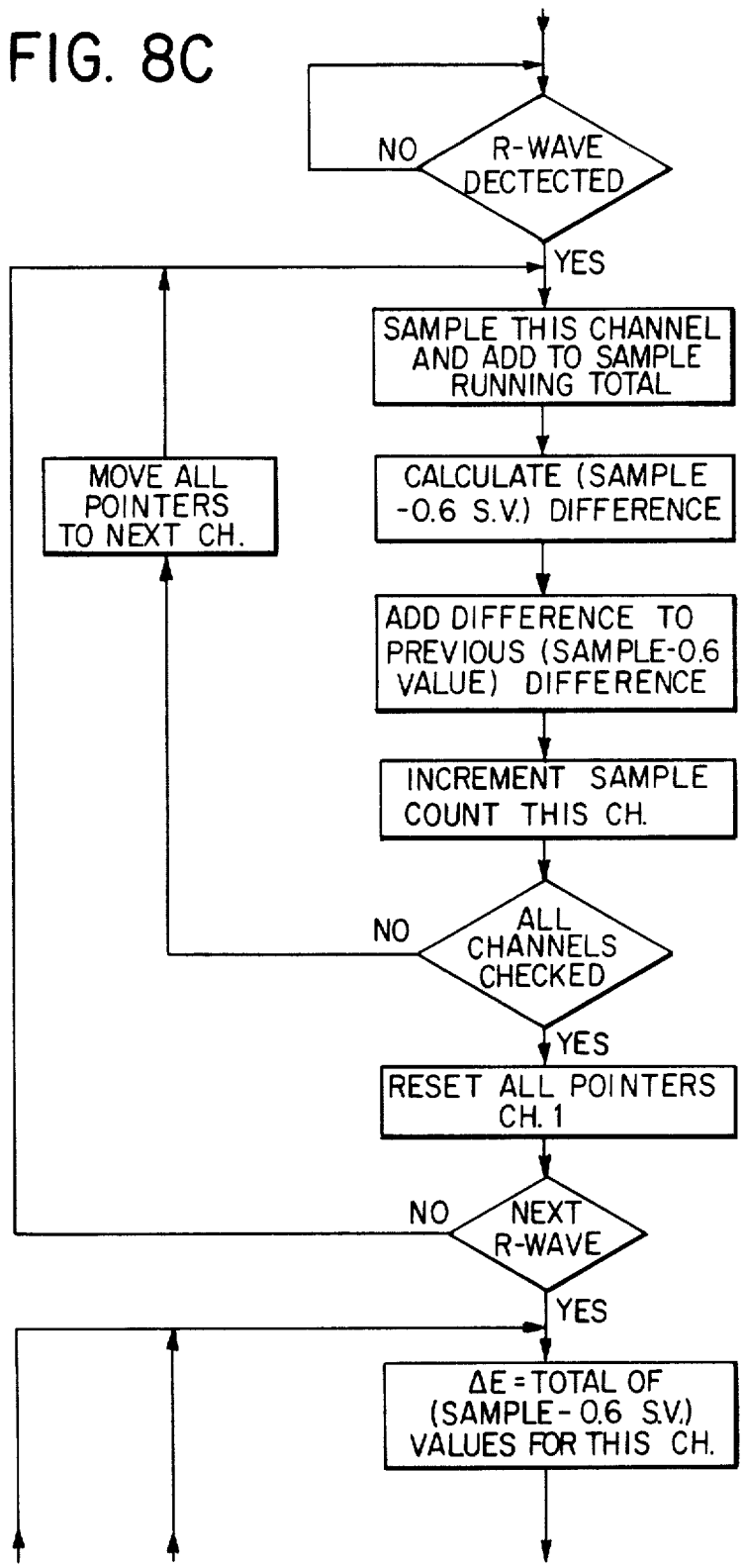

MULTICHANNEL RADIOGRAPHY EMPLOYING SCATTERED RADIATION

DESCRIPTION

1. Technical Field

The present invention concerns a diagnostic imaging system and process. In particular, the invention relates to obtaining data for constructing an image of an interfacial surface in the body using radiation scattered from tissue in the region of the surface. The invention is particularly adapted to obtain data for constructing images of a moving air-tissue interface such as the interface between a beating heart and the lung.

2. Background Art

Diagnostic imaging techniques provide visual images of organs and other structures within the body of a patient and thus are extremely useful diagnostic tools for the medical profession. One such diagnostic imaging technique, termed "computerized axial tomography" (CAT), generally provides images of planar sections of the body of a subject. The CAT technique involves projecting beams of X-ray radiation through the body in many different directions in a plane passing through the body. The degree of absorption of the beams is measured as a function of the direction of the beam. A digital computer collects data specifying the degree of absorbance of the X-ray beam versus the direction of the beam, and with the data computes an image of a cross section of the body through which the plane passed.

Although the CAT technique is routinely used to obtain images of stationary structures within the body, the technique is subject to a number of signficant drawbacks with respect to obtaining an image of a moving structure within the body, such as a beating heart. For example, in CAT instruments commercially available at the present time, X-ray beams are ordinarily projected into the body of a patient for a length of time which spans many heart beats. As a result of the movement of the heart during the time it is exposed to the X-ray beams, the heart appears as a blur in the image. A modified CAT technique has been used to obtain a "stroboscopic" image of a beating heart by sampling the absorbance signals at times synchronized with the heart beats. However, sampled data from many hundreds of heart beats must be accumulated in order to obtain sufficient data with an adequate signal-to-noise ratio to construct a useful image. The resulting stroboscopic image of the heart is therefore a time-averaged image. Short time transient motions of the heart which are not synchronized with the heart beats are generally lost in the averaging process. Furthermore, the patient must remain substantially immobile for several minutes in order to prevent the stroboscopic heart image from becoming blurred.

A research CAT instrument has been constructed which is capable of collecting sufficient data in a time short compared to a single heart beat to construct a "stop-action" image of a beating heart. However, in stop-action images produced with this instrument, the spatial resolution of rapidly moving surfaces of the heart is only roughly 5 millimeters, which is lower than is desired. Another limitation of the instrument is its considerable cost.

Ultrasonic echo techniques are also used to generate images of structures within the body. Furthermore, ultrasonic techniques can be used to obtain images of certain regions of the human heart as the heart is beating. Ordinarily, however, ultrasonics cannot be used to obtain an image of a region of the heart which adjoins an air cavity, since the air-tissue interface gives rise to multiple reflections of ultrasonic waves. The multiple reflections render generation of an image of the air-tissue interface impractical, if not impossible.

An article published by D. G. Tilley et al. in the journal *Medical and Biological Engineering*, volume 14, pages 141–150 (March 1976), discloses a technique for monitoring the motion of a surface which employs radiation scattered from the surface. A collimated beam of X-ray or gamma radiation is projected onto the surface and a detector with a collimated field of view is oriented so that the field of view intersects the beam. The intersection of the collimated beam of radiation and the collimated field of view of the detector defines a region which is termed a "sensitive volume". The presence of material which scatters radiation in the sensitive volume causes radiation to be scattered from the sensitive volume into the detector. Thus it is possible to monitor motion of a surface within the sensitive volume by observing the modulation in the intensity of the scattered radiation. The article discloses that a surface may be scanned by moving the sensitive volume to various locations on the surface and that the technique could be used in evaluating cardiac contractility and elasticity. The article describes experiments in which the motion of a single point on the heart-lung interface of a dog was monitored by the scat- tered-radiation technique. In another experiment, the wave motion of water in a tank several inches in diameter was monitored by detecting the motion of the water surface at five points spaced apart along the diameter of the tank. The instruments disclosed in the article, however, are not suitable for clinical use as a practical matter, since the radiation detectors had to be oriented by hand to position the associated sensitive volumes in intersection with the surface whose motion was to be monitored. This manual orientation procedure is a time-consuming, trial-and-error process which requires a high degree of skill by the operator, since the surface on which the sensitive volumes are to be located in clinical applications are inside the body of a subject and cannot be seen by the operator. The necessity of positioning sensitive volumes on surfaces within the body of a patient by orienting radiation detectors by hand is inconsistent with the clinical requirement of keeping the dosage of X-ray radiation applied to the patient as low as possible.

DISCLOSURE OF THE INVENTION

We have invented a diagnostic imaging system and process which can be used to construct the images of surfaces within the body, including moving surfaces such as the heart-lung interface, which avoids the disadvantages of the prior art discussed above.

Broadly, the invention concerns a diagnostic imaging system for constructing an image of an area of an interfacial surface in the body of a subject. The interfacial surface divides two regions in the body from one another. The contents of the two regions differ in the extent to which they scatter penetrating radiation. For example, the interfacial surface could be a surface of tissue which borders a cavity in the body substantially filled with air, such as the heart-lung interface.

The diagnostic imaging system of the invention includes a radiation source such as an X-ray generator for generating a shaped beam of penetrating radiation. As used herein, the term "penetrating radiation" refers to radiation capable of passing through biological tissue which is substantially opaque to visible light. X-ray radiation and gamma-ray radiation are examples of penetrating radiation. The beam of radiation is preferably fan shaped, although other beam shapes could be used if desired. As used herein, the term "beam of radiation" in the singular is intended to encompass both undivided beams and beams made up of two or more disjoint sub-beams. The radiation source is positioned and oriented to direct the beam into the body of the subject to illuminate a region of the interfacial surface. It is ordinarily preferred for the beam to pass through the interfacial surface and particularly preferred for the beam to be generally normal to the surface.

The diagnostic imaging system also includes a scattered-radiation detector assembly which comprises a detector support frame and two or more directional radiation detectors attached to the support frame. Each directional radiation detector has a directional radiation receptance port which has a limited field of view. A sensitive volume associated with a radiation detector is defined by the intersection of the field of view of the detector with the shaped beam of radiation from the radiation source. Generally the more detectors included in the diagnostic imaging system, the greater the resolution of the image which can be achieved in a single scan. In general it is preferred to have at least three directional radiation detectors. The directional radiation detector produces a radiation intensity signal at an output which is a measure of the intensity of the radiation incident upon the radiation receptance port and propagating in a direction of a range of directions admitted by the receptance port.

The diagnostic imaging system of the invention also includes a sensitive-volume positioning mechanism which permits the locations of the sensitive volumes associated with the directional radiation detectors to be changed individually. Changes in the location of a sensitive volume can be specified by control signals applied to a position control signal input of the mechanism. As explained in detail below, a preferred sensitive-volume positioning mechanism includes apparatus powered by stepping motors for translating the directional radiation detectors as a group and for pivoting certain of the detectors about pivot axes associated with the detectors. However, it will be appreciated that alternate mechanisms for changing the locations of the sensitive volumes are possible and may be preferred for certain applications. For example, the radiation detectors could be independently translatable if desired. A mechanism could be provided for pivoting or translating the radiation beam source, or for altering the shape of the beam.

The diagnostic imaging system of the invention also includes a search-control circuit. The search control circuit preferably includes a microcomputer, although a hardwired logic circuit could be used if desired. The search control circuit is connected to the radiation-intensity signal outputs of each of the directional radiation detectors and to the position control signal input of the sensitive-volume positioning mechanism. The search control circuit is adapted to direct the sensitive-volume positioning mechanism to move selectively each of the sensitive volumes associated with the directional radiation detectors along paths associated with the detectors which intersect the interfacial surface. When a sensitive volume crosses the interfacial surface, the intensity of radiation scattered into the associated directional radiation detector changes and thus the radiation intensity signal from the detector changes. The search control circuit is adapted to monitor the radiation intensity signal from each directional radiation detector as the sensitive volume associated with the detector is moved and to stop the sensitive volume at an operating position at which the radiation intensity signal from the detector, or an average value of the radiation intensity signal, at least approximately equals an operating point value associated with the detector. The operating point value of the radiation intensity signal corresponds to locating the sensitive volume associated with the detector in a position straddling the interfacial surface.

The system further includes image-construction means capable of constructing an image of an area of the interfacial surface from data which specifies the relative locations of the operating positions of the directional radiation detectors.

In preferred embodiments of the diagnostic imaging system of the present invention, the support frame of the scattered radiation detector assembly can be moved along a search path. The search path is preferably a straight line extending generally parallel to the radiation beam. Such preferred embodiments further include a support-frame drive motor connected to the support frame which is capable of advancing the support frame along the search path in response to support-frame drive signals applied to an input of the support-frame drive motor. One of the detectors in such preferred embodiments defines a principal radiation detector. The principal radiation detector can be rigidly secured to the support frame to have a fixed orientation relative to the frame. The remaining radiation detectors are pivotably attached to the support frame. Pivot drive motors are provided for rotating the pivotable radiation detectors. The search control circuit of such preferred embodiments is adapted to direct the support-frame drive motor to advance the support frame along the search path to cause the sensitive volume associated with the principal radiation detector to intersect the interfacial surface and to direct the pivot drive motors to rotate each of the pivotable radiation detectors to cause the sensitive volumes associated with the pivotable radiation detectors to intersect the interfacial surface. The search control circuit of such embodiments is further adapted to monitor the radiation intensity signals from the radiation detectors and to stop the advance of the support frame and the rotation of the pivotable radiation detectors in a condition in which an average value of the radiation intensity signal from each radiation detector at least approximately equals an operating point value which corresponds to locating the sensitive volume associated with the detector in a position straddling the interfacial surface.

A feature of the diagnostic imaging system of the present invention is that the sensitive volumes associated with the directional radiation detectors can be automatically and swiftly positioned on an interfacial surface in the body, such as a heart-lung interface, to permit data for constructing an image of an area of the surface to be collected. The time required to locate the sensitive volumes on the surface is sufficiently short to keep the radiation exposure to the patient well below recommended limits.

A second feature of the present invention is that the relative positions of the sensitive volumes associated with the directional radiation detectors can be used to construct an image of an interfacial surface which need not be limited to a planar cross-sectional view.

Another feature of the present invention is that the modulation of the radiation intensity signals from the directional radiation detectors provides information concerning the movement of the interfacial surface. Thus, for example, motion of an interfacial surface of a beating heart can be monitored and imaged, effectively in real time.

Interfacial surfaces between air and a tissue are generally more effectively characterized by the imaging system of the present invention than interfacial surfaces separating two different types of tissue. Consequently, the diagnostic imaging system of the present invention complements ultrasonic imaging instruments, which, as noted above, are limited in their ability to image air-tissue interfaces.

The present invention is a particularly helpful diagnostic tool for the medical profession. It is a noninvasive technique for obtaining data for constructing visual images of surfaces within the body which cannot ordinarily be seen. The apparatus of the invention does not require a highly skilled operator and can produce finely resolved images with low dosages of radiation. Moreover, it is expected that commercial embodiments of the invention will be significantly less costly to manufacture than the CAT systems presently available.

BRIEF DESCRIPTION OF THE DRAWINGS

The details of preferred embodiments of the invention will be described in connection with the accompanying drawings.

FIG. 3 is a side view in partial section of an X-ray source and a scattered radiation detector assembly of a preferred embodiment of the present invention.

FIG. 7 is a partial cutaway view taken along line 7—7 of FIG. 3.

FIGS. 8A–D taken together are a flow diagram of a preferred search procedure carried out by the diagnostic imaging system of FIG. 6.

BEST MODE FOR CARRYING OUT THE INVENTION

Figure 1:
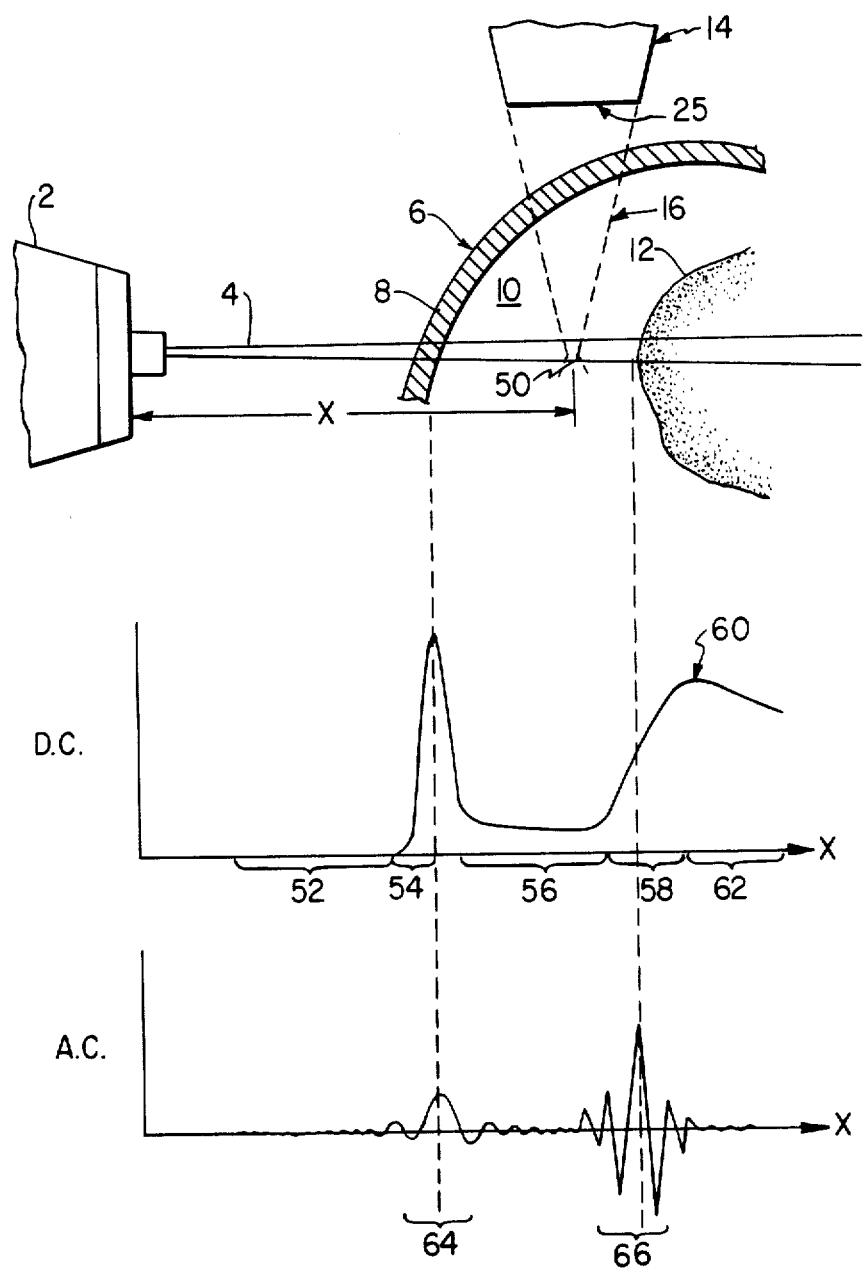
FIG. 1 is a schematic side view in partial section of an X-ray source and directional X-ray detector of the present invention in operation, together with schematic graphs of DC and AC components of a radiation intensity signal from the detector as a function of the position of the detector above the chest of a subject.

Turning now to FIG. 1, an X-ray source 2 produces a shaped X-ray beam 4 which is projected into the body of a subject 6. The beam 4 passes through a thoracic wall 8, a lung cavity 10, and a heart 12 of the subject. A directional X-ray detector 14 is spaced apart from the X-ray beam 4 and has a collimated field view 16 which intersects the X-ray beam 4. A preferred directional X-ray detector 14 of the invention is illustrated in FIG. 2.

Figure 2:
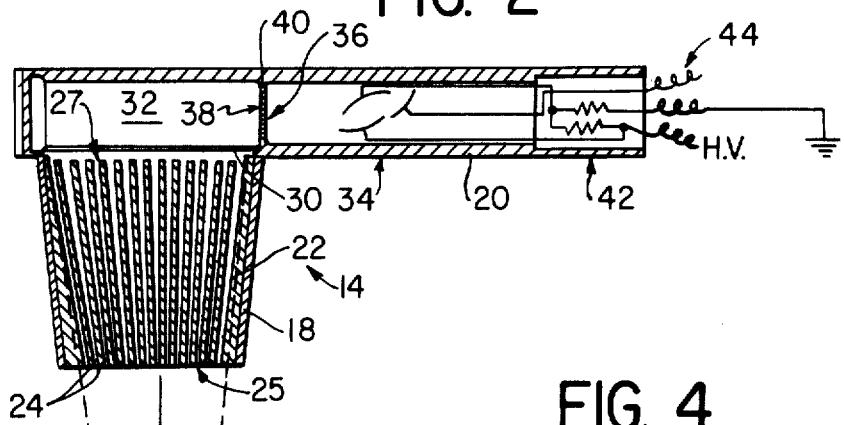
FIG. 2 is a cross-sectional side view of a preferred directional radiation detector of the present invention.

As shown in FIG. 2, a directional X-ray detector 14 includes a collimator assembly 18 attached to a detector housing 20. The collimator assembly 18 includes a collimator block 22 made of lead. A plurality of passageways 24 extend through the collimator block 22 from a collimator entrance face 25 to a collimator exit face 27. One detector of the present invention has 117 passageways 24. Each passageway 24 is substantially straight to define a passageway axis. Each passageway 24 is generally circular in cross section and is tapered substantially linearly from a diameter of about 1.3 mm at one end to a diameter of about 2.0 mm at the opposite end. The larger ends of the passageways 24 pass through the collimator exit face 27 of the lead block 22. The walls between the adjacent passageways 24 are about 0.5 mm thick in their thinnest dimension. The collimator assembly 18 is roughly 64 mm thick from the entrance face 25 to the exit face 27.

The passageways 24 are oriented so that the axes of the passageways approximately coincide at a point which defines a focal point 26 of the collimator 18. The focal point 26 of collimator assembly 18 is located about 120 mm in front of the collimator entrance face 25. A focal plane 28 is defined by a plane passing through the focal point 26 and normal to an average direction of the axes of the passageways 24 of the collimator 18. A field of view axis 29 is defined by a line extending normal to the focal plane 28 and passing through the focal point 26. A field of view defined by each passageway 24 individually converges to a disc approximately centered at the focal point 26 and approximately lying in the focal plane 28 of the collimator 14. The passageways 24 of the collimator assembly 18 thus cooperate to limit the field of view of the directional X-ray detector 14. The effective diameter of the field of view 16 of the directional X-ray detector 14 in the focal plane 28 is roughly 5 mm.

The collimator exit face 27 of the collimator assembly 18 is located adjacent to an aluminum foil light seal 30. Located within the detector housing 20 adjacent to the aluminum foil light seal 30 is a thallium-activated sodium iodide scintillation crystal 32. The scintillation crystal is generally cylindrical in shape about 51 mm long and about 13 mm in diameter. The crystal is commercially available as a "Type 2D8" thallium-activated sodium iodide crystal from Harshaw Chemical Co. of Solon, Ohio. A photomultiplier tube 34 is located in the detector housing 20 and extends generally perpendicular to the collimator field of view axis 29. A suitable photomultiplier tube for this application is a photomultiplier tube designated model DM-3242 availabe from Thompson CSF, Inc. of Clifton, N.J. An optical input port 36 of the photomultiplier tube 34 is located adjacent to a scintillation output face 38 of the scintillation crystal 32. A layer of optical coupling grease 40 couples the scintillation output face 38 of the scintillation crystal 32 to the optical input port 36 of the photomultiplier tube 34. The aluminum foil light seal 30 is joined to the detector housing 20 in a light-tight manner and serves to prevent stray light from falling on photomultiplier tube 34. A voltage divider circuit 42 is located in the detector housing 20 for deriving a series of voltages for the dynodes of the photomultiplier tube 34 from a high voltage applied across the voltage divider. The voltage divider circuit 42 is positioned in the base of the photomultiplier tube 34. A photocurrent output connector of the photomultiplier tube 34 defines a radiation-intensity signal output 44 of the directional radiation detector 14.

Turning again to FIG. 1, the intersection of the field of view 16 of the directional radiation detector 14 with the shaped X-ray beam 4 from the X-ray source 2 defines a sensitive volume 50. Material which scatters X-ray radiation which is present in the sensitive volume 50 causes X-ray radiation to be scattered from beam 4 into the collimator entrance port 25 of the X-ray detector 14. Moving the sensitive volume 50 from outside the thoracic wall 8 to within the tissue of the heart 12 of the subject 6 gives rise to a radiation intensity signal which varies as a function of the position of the sensitive volume. Representative DC and AC components of such a radiation intensity signal are shown in FIG. 1.

When the sensitive volume 50 is located outside of the body of the subject, the radiation intensity signal is extremely low, since air scatters X-ray radiation only slightly. Thus, since the region 52 of the graph of the DC component in FIG. 1 corresponds to location of the sensitive volume 50 outside of the body, the level of the DC component in region 52 is essentially a base-line value. When the volume 50 intersects and passes into the thoracic wall 8, as in region 54 of the graph, a sharp increase in the DC component of the radiation intensity signal is observed. As the sensitive volume 50 withdraws from the thoracic wall 8 and passes into the lung cavity 10, the DC component of the radiation intensity signal drops to a relatively low value, since the lung cavity 10 is filled principally with air. See region 56 of the graph. The gradual decrease in the DC component of the radiation intensity signal shown in region 56 of the graph is caused principally by a gradual reduction of the intensity of the beam 4 as it passes through the lung cavity 10. The reduction in beam intensity is caused by partial absorption of the beam radiation by lung tissue and by scattering of radiation from the beam by such tissue. As the sensitive volume 50 passes into the tissue of the heart, the DC component of the radiation intensity signal increases over the region 58 to a local maximum value 60 and then decreases to a degree in the region 62. The increase in the signal in the region 58 is due to the scattering of X-ray radiation by the tissue of the heart 12. The decrease observed in region 62 as the sensitive volume 50 passes further into the heart is due to the absorbance of the scattered radiation by heart tissue which lies within the field of view 16 of the detector 14.

The movement of the heart 12 caused by its beating gives rise to an AC component of the radiation intensity signal, a representative graph of which is shown in FIG. 1. The AC component is observed most strongly when an air-tissue interface falls within the sensitive volume 50, as in regions 64 and 66 of the graph of the AC component in FIG. 1. When an air-tissue interface which passes through a sensitive volume moves so as to change the quantity of scattering material in the sensitive volume, the intensity of the radiation scattered into the detector 14 changes, which in turn leads to a change in the radiation intensity signal produced by the detector. Substantially periodic motion by the interface such as caused by a beating heart can therefore give rise to an AC component of the radiation intensity signal.

Turning now to FIG. 3, a diagnostic imaging system 70 of the present invention includes an X-ray beam source 72 capable of producing a beam of X-rays. The X-ray beam source 72 includes an X-ray generator 73 such as a generator designated "Model 1DB13A1 Heavy Duty Maxiray-125 X-ray Unit," available from the General Electric Company. The X-ray generator 73 is fitted with a beam collimator 74 which is attached to a face plate 76 of the generator. The beam collimator 74 collimates the X-ray beam to a fan shape. It is convenient in connection with describing the apparatus of FIG. 3 to define a coordinate system having an x axis directed along the center of the fan-shaped X-ray beam produced by the beam source 72, a z axis in the plane of the paper of FIG. 3, and a y axis extending out of the plane of the paper. A cross section of the fan-shaped X-ray beam taken perpendicular to the x direction is roughly rectangular in shape, having a thickness dimension in the z direction which is substantially less than its widthwise dimension in the y direction. At the nominal position of the surface to be imaged, the beam is roughly 10 mm thick and roughly 70 mm wide.

A scattered radiation detector assembly 80 is attached to the X-ray beam source 72 by a support structure 82. The detector assembly 80 is spaced apart from the X-ray beam in the z direction. The scattered radiation detector assembly 80 includes a detector support carriage 84 to which are attached seven directional X-ray detectors 101-107 of the type described above in connection with FIG. 2. The detector support carriage 84 serves as a support frame for the directional radiation detectors. The seven directional X-ray detectors are disposed relative to one another as illustrated schematically in FIGS. 3 and 4.

Figure 4:
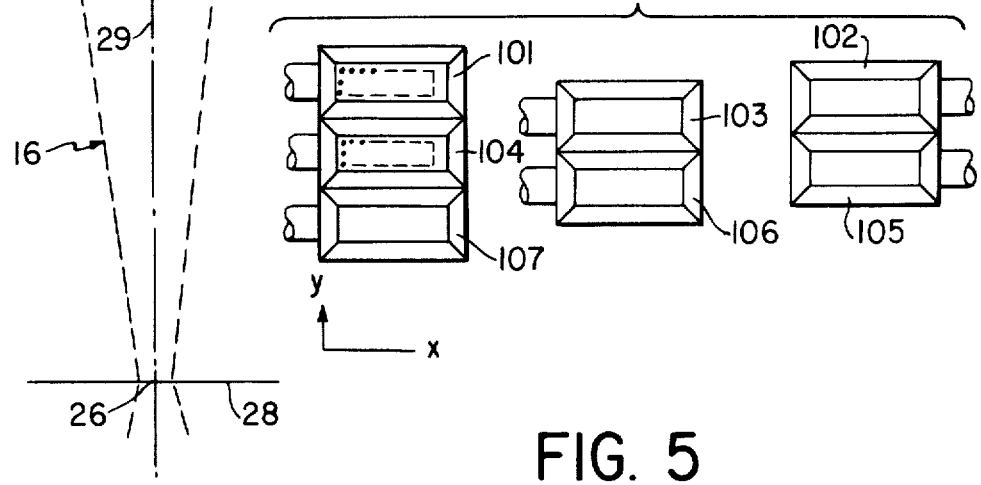
FIG. 4 is a schematic view from below of the directional X-ray detectors of the scattered radiation detector assembly of FIG. 3.
Figure 5:
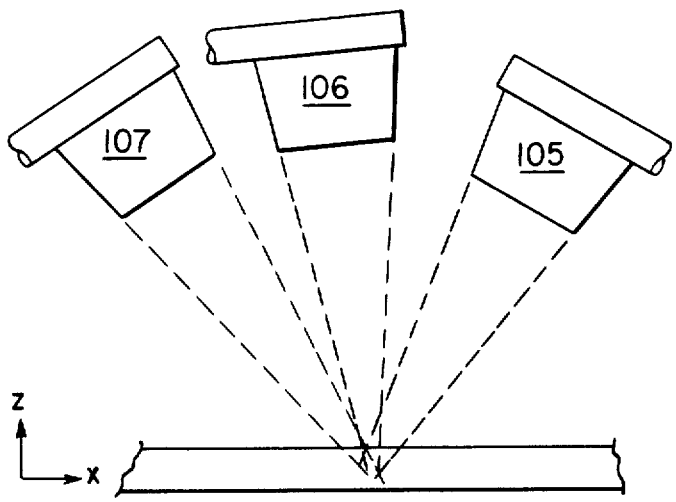
FIG. 5 is a simplified schematic side view of the directional X-ray detectors of the scattered radiation detector assembly of FIG. 3.

As shown in FIG. 4, the seven directional detectors 101-107 are arranged in an array consisting of three rows, a first row having three detectors 101, 104, 107 disposed side by side, a second row having two detectors 103, 106 disposed side by side, and a third row having the remaining two detectors 102, 105 disposed side by side. The X-ray detectors 101-107 are offset from one another in the y direction by about 10 mm. The seven directional X-ray detectors can be oriented so that the seven associated sensitive volumes approximately fall on a single straight line extending in the y direction, as shown in FIG. 5. Because the X-ray detectors 101-107 are offset from one another in the y direction by a distance greater than the effective diameters of the sensitive volumes, the sensitive volumes do not overlap significantly when they are located on the line.

One of the seven directional X-ray detectors defines a principal X-ray detector 104. The principal X-ray detector 104 is rigidly attached to the support carriage 84. Each of the remaining six directional X-ray detectors 101, 102, 103, 105, 106, 107 is pivotable about a pivot axis associated with the detector. Connected to each of the pivotable X-ray detectors 101, 102, 103, 105, 106, 107 is a corresponding pivot drive stepping motor 111, 112, 113, 115, 116, 117. A suitable stepping motor for this application is model K82227-P2 stepping motor available from North American Phillips of Cheshire, Conn.

Turning now to FIG. 7, the pivot drive stepping motor 115 has a drive shaft which is connected to the directional X-ray detector 105 by means of a 10:1 speed-reducing, antibacklash gear train 125. A gear train 125 made up of model No. 8P72X-220 antibacklash gear and model No. P72513-22 precision spur gear available from Winfred Burg, Inc. of East Rockaway, N.Y. is suitable. Rotation of the drive shaft of the stepping motor 115 causes the X-ray detector 105 to pivot about the pivot axis. The pivot drive stepping motor 115 is an electrically controlled motor which permits the angle of orientation of the X-ray detector 105 to be precisely controlled. The angle of orientation of the pivotable X-ray detector 105 may be set to within about plus or minus 0.02 degrees. The remaining five pivotable directional detectors are similarly connected to pivot drive motors by antibacklash gear trains and can be oriented with substantially the same precision.

The detector support carriage 84 is translatably mounted on a carriage track 130. A carriage drive head is connected to the support carriage 84 and engages the threads of a lead screw 134 so that rotation of the lead screw 134 in one direction or the other causes the support carriage 84 to advance in one direction or the other along the carriage track 130. The lead screw 134 is connected to a carriage-drive stepping motor 136. The carriage drive stepping motor 136 is electrically controlled and, in combination with the lead screw 134 and the carriage drive head 132, permits the detector support carriage 84 to be positioned along the carriage track 130 to within about plus or minus 0.025 mm. A stepping motor and translating carriage assembly available under the trade names of "Slo-Syn-Stepper Motor" and "Unislide Assembly" from Velmex, Inc. of East Bloomfield, N.J. function suitably for this application.

Figure 6:
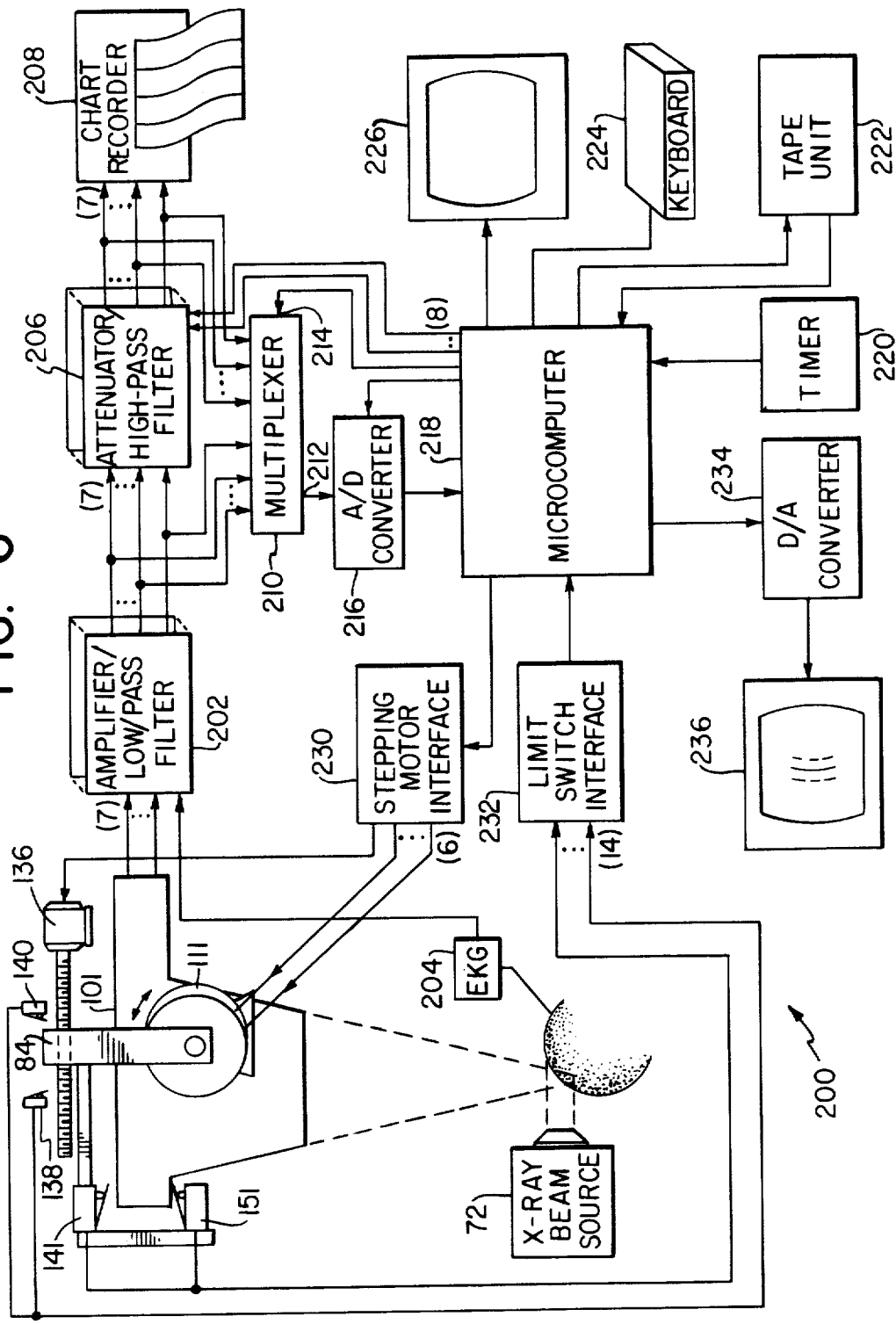
FIG. 6 is a block diagram of a preferred diagnostic imaging system of the present invention incorporating the preferred apparatus of FIG. 3.
Figure 8A:
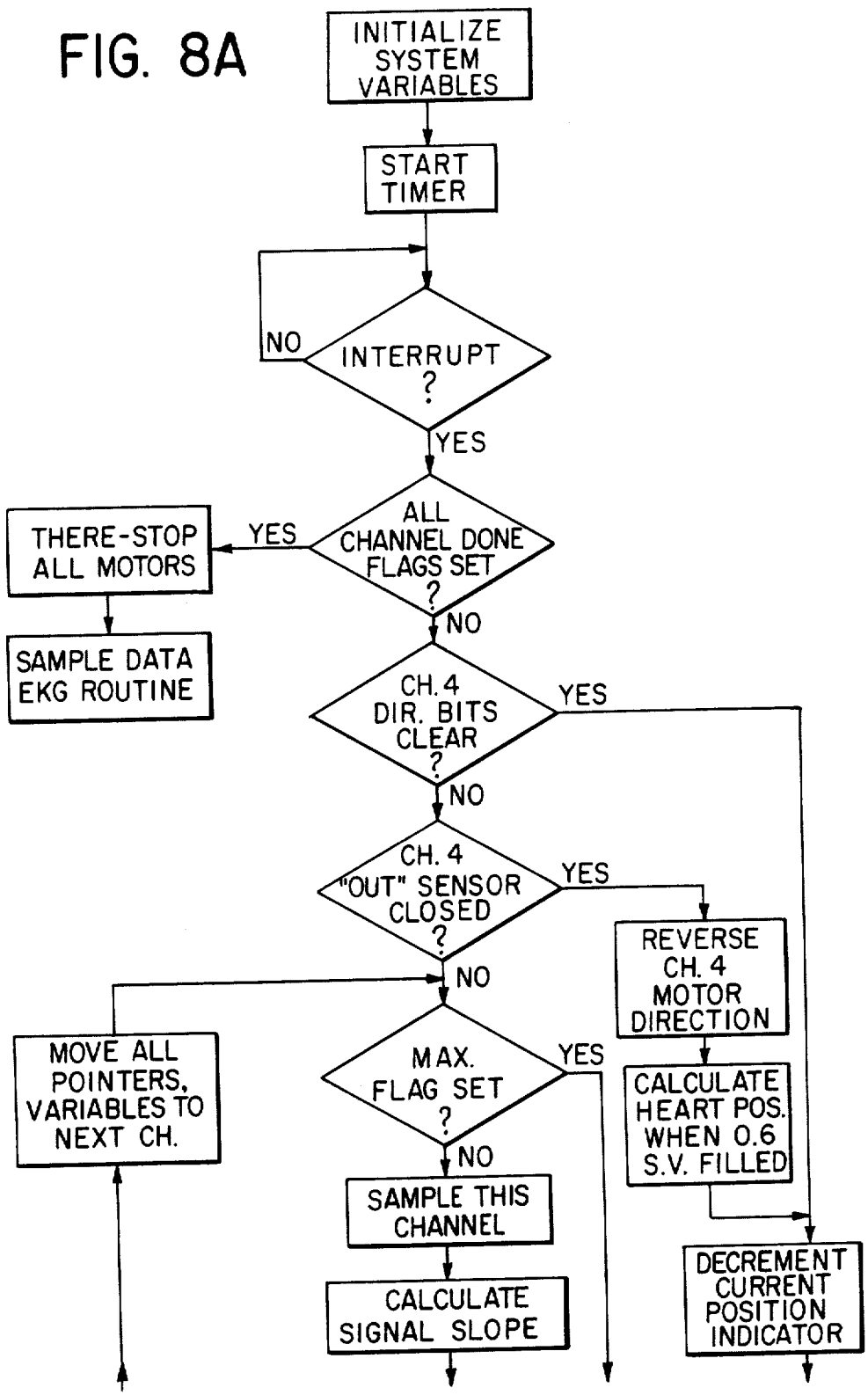
Figure 8D:
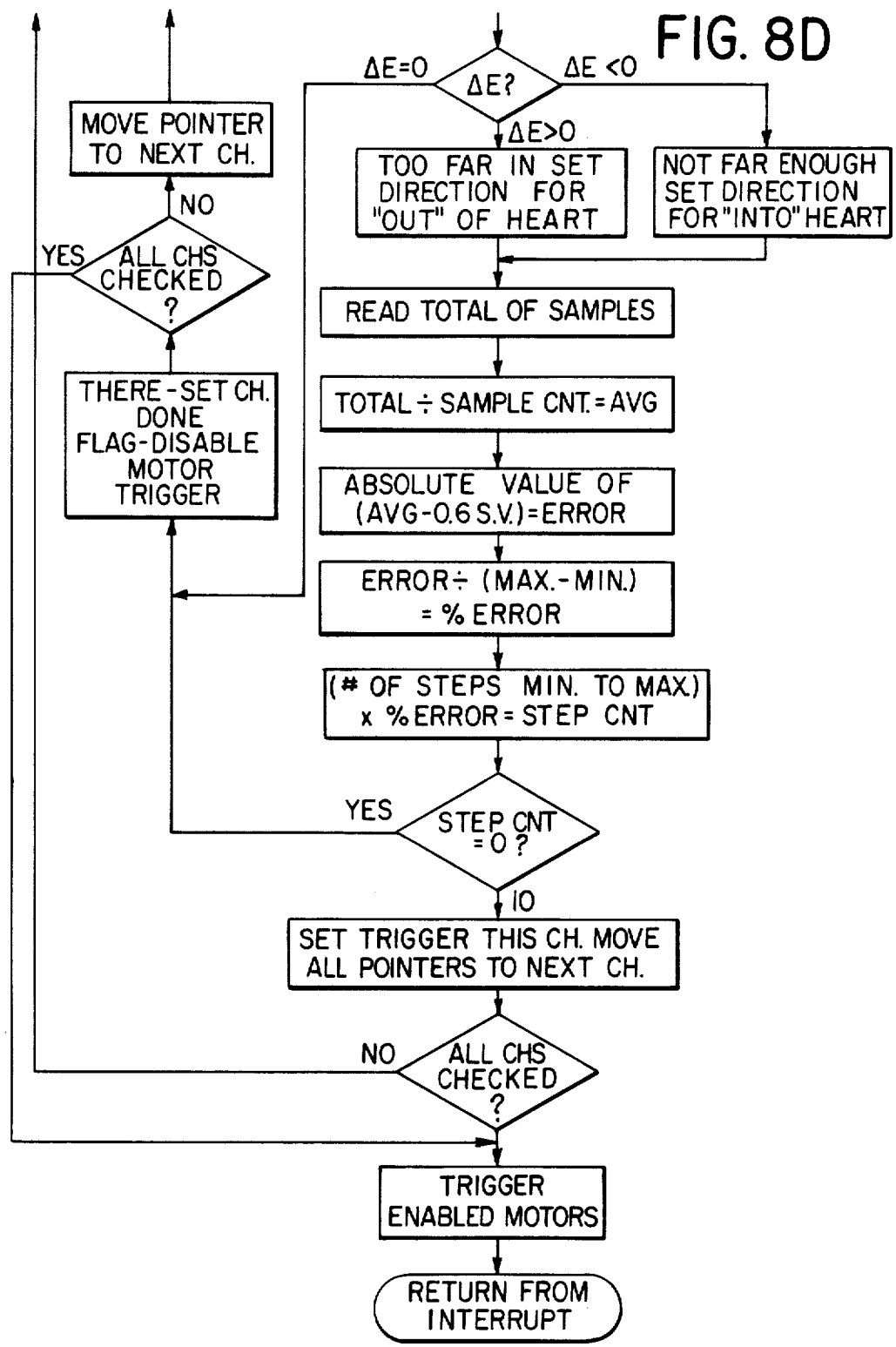

A block diagram of a preferred diagnostic imaging system 200 of the present invention is shown in FIG. 6. The imaging system 200 incorporates the apparatus illustrated in FIG. 3. For simplicity, only one directional X-ray detector 101 is shown. The radiation intensity signal output of each of the seven X-ray detectors 101-107 is connected to an input of a corresponding one of seven low-pass filter/amplifiers 202. An electrocardiogram unit 204 which can monitor electrocardiogram signals from the heart of a subject is connected to an eighth low-pass filter/amplifier 202. The outputs of the eight low-pass filter/amplifiers 202 are connected in turn to the inputs of eight high-pass filter/attenuators 206. The degree of attenuation of each of the high-pass filter/attenuators 206 is digitally programmable and can be set by a digital control signal applied to an attenuation control signal input of the high-pass filter/attenuator 206. The outputs of the high-pass filter/attenuators 206 are connected to the inputs of an eight-channel strip chart recorder 208. The strip-chart recorder 208 can record on a single time axis AC components of the electrocardiogram signal from a subject and AC components of the radiation intensity signals from the seven directional X-ray detectors 101-107.

The outputs of the low-pass filter/amplifiers 202 and the outputs of high-pass filter/attenuators 206 are connected to the inputs of a sixteen-channel analog multiplexer 210. The analog multiplexer 210 can selectively connect one of its sixteen inputs to an output 212 in response to a digital channel select signal applied to a channel-select input 214. The output 212 of the analog multiplexer 210 is connected to an analog-signal input of an analog-to-digital converter 216. The digital output of the analog-to-digital converter 216 is connected to an input port of a microcomputer 218.

The microcomputer 218 includes the following components: a central processing unit (CPU), a read-only memory (ROM), a random-access memory (RAM), and interface circuits for a keyboard, a CRT display, and a tape unit. Suitable components are available, for example, from Motorola, Inc. of Phoenix, Arizona as elements of their "M68-ADS-2A" computer system. A crystal controlled digital timer 220 is connected to the microcomputer 218 to provide timing signals. A magnetic tape unit 222 is connected to the microcomputer 218 to provide bulk data storage. A keyboard 224 and an alphanumeric CRT display monitor 226 are connected to the microcomputer 218 to provide an input/output terminal for instructions and data. The operating principles and preferred interconnection of elements of the "M68-ADS-2A" computer system are described fully in literature readily available from Motorola, Inc. Consequently, the operation of the microcomputer 218 will not be described in detail here.

A stepping motor interface circuit 230 is connected to an output of the microcomputer 218 and to the six pivot-drive stepping motors 111, 112, 113, 115, 116, 117 and to the carriage drive stepping motor 136. The stepping motor interface circuit 230 translates a digital command by the microcomputer 218 directed to a specified one of the seven stepping motors to rotate clockwise or counterclockwise one step into a motor drive signal transmitted to the specified stepping motor to cause the motor to rotate one step in the direction specified. The microcomputer 218 can therefore control the rotation of the stepping motors 111, 112, 113, 115, 116, 117, 136 one step at a time to pivot in either direction any of the pivotable directional radiation detectors 101, 102, 103, 105, 106, 107 of the scattered radiation detector assembly 80 and to translate in either direction the support carriage 84 of the assembly 80.

Limits for the rotation of each of the pivotable X-ray detectors 101, 102, 103, 105, 106, 107 are set by pairs of pivot limit switches associated with each pivotable detector. Taking the X-ray detector 101 shown in FIG. 6 as an example, a first pivot limit switch 141 and a second pivot limit switch 151 are fixed to the detector support carriage 84. The first pivot limit switch 141 is located such that when the detector 101 is rotated to a first limit orientation, it contacts and depresses the first pivot limit switch 141. The second pivot limit switch 151 is similarly depressed when the X-ray detector 101 is rotated to a second limit orientation. The first and the second pivot limit switches restrict the rotation of the detector to a swing of about 20°. The first and the second pivot limit switches 141 and 151 are connected to a limit-switch interface circuit 232, which in turn is connected to an input port of the microcomputer 218. The limit switch interface circuit 232 generates a digital signal which identifies any limit switch which is depressed. Thus, when the microcomputer 218 rotates a pivotable X-ray detector to a pivot limit orientation, it receives a signal from the limit switch interface circuit 232 which warns that the limit orientation has been reached.

Limits for the translation of the support carriage 84 are similarly set by a pair of translation limit switches 138 and 140. A first and a second translation limit switch 138 and 140 are mounted on the detector assembly support structure 82 (not shown in FIG. 6) in positions such that they are contacted and depressed by the detector support carriage 84 when the support carriage 84 reaches a first or a second limit. The first and the second limit positions are separated by roughly 100 mm. The first and the second translation limit switches 138 and 140 are connected to the limit-switch interface 232. Consequently, when the support carriage 84 is moved to the first or the second limit position, the microcomputer 218 receives a signal indicating that the limit position in question has been reached.

For each pivotable X-ray detector, the microcomputer 218 maintains a detector orientation count in memory. When a detector is placed at the first pivot limit orientation, the corresponding detector orientation count is cleared to zero. For each step the associated pivot drive stepping motor rotates the detector in question away from the first pivot limit orientation, the detector orientation count is incremented by one. For each step the associated pivot drive stepping motor rotates the detector in question back towards the first pivot limit orientation, the detector orientation count is decremented by one. Thus, at any time the detector orientation count corresponding to a pivotable X-ray detector equals the number of steps the stepping motor associated with the detector must make to return the detector to the first pivot limit orientation. Since the increment of rotation of a pivotable X-ray detector about its pivot axis caused by a single step of the associated pivot drive stepping motor is known, a detector orientation count digitally encodes the angle between the current orientation of the corresponding pivotable detector and its first pivot limit orientation. The current linear position of the support carriage 84 along the track 130 relative to the first limit position defined by the first translation limit switch 138 is digitally encoded in the microcomputer 218 in an analagous manner.

The microcomputer 218 is connected to attenuation-control signal input of the eight high-pass filter/attenuators 206 to permit the degree of attenuation of the signals passing through the high-pass filter/attenuators to be set by the computer. The AC components of the radiation intensity signals can thus be normalized relative to the variation observed in the corresponding DC components as the associated sensitive volumes pass through the interfacial surface of interest from a first region to a second region in the body. The variation in an AC component thus normalized approximately measures the extent to which the intervacial surface moves through the corresponding sensitive volume.

A video display unit 236 is connected to the microcomputer 218 by means of a digital-to-analog converter 234. The video display unit 236 can display an image specified by the microcomputer 218, such as the image of a surface calculated to fit data obtained from the orientations of the six pivotable X-ray detectors 101, 102, 103, 105, 106, 107 and from the radiation-intensity signals from the six pivotable X-ray detectors and the principal X-ray detector 104.

The diagnostic imaging system 200 described above can resolve features on the heart-lung interface which have dimensions greater than roughly 5 mm. This resolution limit is set by the dimensions of the sensitive volumes associated with the directional radiation detectors, since for a given type of scattering material the intensity of radiation scattered from a sensitive volume depends primarily on the quantity of the scattering material located in the sensitive volume and does not depend to a significant extent on the shape of the material within the sensitive volume. However, a spatially-averaged position can be defined for each sensitive volume by assuming that the sensitive volume is filled with material of uniform density to a level which defines the spatially-averaged position. Changes in this spatially-averaged position can be resolved to within about plus or minus 0.1 mm by the diagnostic imaging system 200. Thus motion of spatially-averaged positions on the interfacial surface of interest can be resolved to within about plus or minus 0.1 mm.

A preferred method for operating the diagnostic imaging system discussed above to collect data for constructing an image of an area of a heart-lung interface in the body of a subject will now be described. A preliminary fluoroscopic examination of the chest of the subject may be carried out if necessary to locate the lung cavity and the approximate position of the area of interest of the heart-lung interface. The subject is positioned supine in front of the X-ray beam source 72 with the scattered-radiation detector assembly 80 located generally above the area of the heart-lung interface of interest. The scattered radiation detector assembly 80 is placed in a pre-search condition by the microcomputer 218. Specifically, the pivotable X-ray detectors 101, 102, 103, 105, 106, 107 are rotated to pre-search orientations which bring the focal points of all seven X-ray detectors 101-107 into approximate alignment in the y direction, as discussed above in connection with FIG. 5. The first and the second pivot limit switches associated with each pivotable X-ray detector are set so that the detector can pivot about plus or minus 10° from the pre-search orientations. The detector support carriage 84 is moved to a pre-search position. The subject is located so that the focal points of the X-ray detectors thus aligned and positioned in the pre-search state fall within the lung cavity of the subject, displaced roughly 30 mm from the area of the heart-lung interface.

A fan-shaped beam of X-ray radiation is directed from the beam source 72 into the chest of the subject and through the heart-lung interface. The microcomputer 218 then directs the support carriage 84 to be advanced along the track 130 from the pre-search position to the second limit position so that the sensitive volumes associated with the seven directional X-ray detectors 101-107 approach, traverse, and withdraw from the lung-heart interface. As the support carriage 84 is being moved, the radiation intensity signals from the seven directional X-ray detectors are monitored by the microcomputer 218. For each detector a minimum value of the radiation intensity signal is determined, along with the location of the support carriage 84 at which the minimum value occurred. A minimum value of the radiation intensity signal generally occurs when the corresponding sensitive volume is located within the lung cavity, but adjacent to the lung-heart interface. See FIG. 1. Similarly, a maximum value of the radiation intensity signal is determined for each detector along with the position of the support carriage 84 at which the maximum value occurred. A maximum value of the radiation intensity signal generally occurs when the corresponding sensitive volume is located within the heart tissue, but adjacent to the lung-heart interface, as illustrated in FIG. 1. The support carriage 84 can be moved from the pre-search position to the second limit position in roughly 3 sec. The variation in the radiation intensity signals from detectors caused by heart beats occuring during the time the support carriage 84 is in motion is generally sufficiently small compared to the DC component of the signal that the variation can be ignored in determining the minimum and the maximum values.

After the minimum and the maximum values of the radiation intensity signal from the principal radiation detector 104 have been determined, the microcomputer 218 calculates a trial base location for the detector support carriage 84. The trial base location is the calculated midpoint between the positions at which radiation intensity signal from the principal radiation detector 104 attained the minimum and the maximum values. After the trial base location of the detector support carriage 84 has been calculated, trial orientations for each of the pivotable directional X-ray detectors 101, 102, 103, 105, 106, 107 are calculated by the microcomputer 218. The trial orientation is specified to be the angle for which the sensitive volume associated with the detector will be located at a position approximately midway between the positions at which the radiation intensity signal from the detector attained the maximum and the minimum values when the support carriage 84 is located at the trial-base position.

The microcomputer 218 directs the support carriage 84 to be moved to the trial base location and pivots each pivotable directional X-ray detector 101, 102, 103, 105, 106, 107 to the trial orientation associated with the detector. The pivoting of the pivotable detectors is carried out simultaneously with the translation of the support carriage 84.

The microcomputer 218 calculates an operating point value for each X-ray detector. The operating point value for an X-ray detector is defined to be the sum of the minimum value found previously for the radiation intensity signal from the detector and the product of 0.6 times the difference between the previously found maximum value and the minimum value.

After the detector support carriage 84 reaches the trial-base location, the position of the support carriage is trimmed by moving it to a position at which a time-averaged radiation intensity signal from the principal X-ray detector substantially equals the operating point value associated with the detector. The resulting position defines an operating base position of the detector support carriage 84.

The microcomputer 218 computes the time-averaged radiation intensity signal by the following procedure. By transmitting control signals to the multiplexer 214 and the analog-to-digital converter 216, the microcomputer 218 directs that the radiation intensity signal from the principal X-ray detector 104 be digitized at periodic intervals spaced by a time, such as 20 msec, which is much shorter than a heart beat. During a single heartbeat cycle, a running sum of the digitized values of the radiation intensity signal is computed by the microcomputer 218 and the number of summands making up the sum is counted. The duration of a heart beat can be determined by the microcomputer 218 from an electrocardiogram signal produced by the electrocardiogram unit 204. After the completion of the heart beat cycle, the final sum of the digitized values of the radiation intensity signal is divided by the number of summands to yield an average value of the radiation intensity signal from the principal X-ray detector over the time of the heart beat.

After the detector support carriage 84 reaches the operating base position, the angle of each of the pivotable X-ray detectors 101, 102, 103, 105, 106, 107 is trimmed by rotating the detector so that a time-averaged radiation intensity signal from the detector substantially equals the operating point value corresponding to the detector. The time-averaged radiation intensity signal from the pivotable X-ray detectors is computed by the microcomputer 218 in an exactly analagous procedure to that described in the preceeding paragraph for the time-averaged radiation intensity signal from the principal radiation detector. Each pivotable X-ray detector is thus placed in an orientation which defines an operating orientation of the detector.

The microcomputer 218 at this point has the operating orientations of the six pivotable directional X-ray detectors 101, 102, 103, 105, 106, 107 stored in its memory. The six operating angles together with data permanently stored in the computer memory specifying x and z coordinates locating the pivot axis of each pivotable X-ray detector, and the offset distances between the pivotable X-ray detectors in the y direction constitute geometrical data sufficient to specify the locations of the sensitive volumes associated with the pivotable X-ray detectors on the heart-lung interface. The z coordinates of each pivot axis is measured relative to an x-y midplane of the fan-shaped X-ray beam and thus specifies the height of the pivot axis above the beam. The pivot axes generally extend parallel to the y direction. From this geometrical data an image of the heart lung interface can be calculated by the microcomputer 218 and displayed on the video display unit 236. The motion of the heart can be monitored by monitoring the modulation of the radiation intensity signals from the X-ray detectors when the detector support carriage 84 is in the operating base position.

The microcomputer 218 can be programmed to direct the diagnostic imaging system 200 to collect data for imaging an area of a heart-lung interface as described above. A flow diagram of such a program is presented in FIGS. 8A–8D, taken together. The abbreviation "S.V." in the flow diagram refers to "sensitive volume." The "R-wave" referred to in the flow diagram is a signal from the electrocardiogram unit 204 which tracks the cardiac cycle. Each pivotable X-ray detector 101, 102, 103, 105, 106, 107 and its associated pivot-drive stepping motor 111, 112, 113, 115, 116, 117 is referred to in the flow diagram as a channel. The principal directional X-ray detector 104 and the carriage-drive stepping motor 136 is referred to as channel 4. The flow diagram of FIGS. 8A–8D is self-explanatory and will not be described further.

The lead collimator block 22 of the collimator assembly 18 of the directional X-ray detector illustrated in FIG. 2 can be made by a casting process described below which uses tapered steel pins to mold the collimator passageways 24 discussed above in connection with FIG. 2. Pin blanks for the required number of passageways 24 for the collimator block 22 are machined on a lathe from ⅛ in (3.2 mm) steel rod stock. The pin blanks have uncut end stubs at both ends and a generally tapered central section about 66 mm long which tapers from a diameter of about 1.3 mm at one end to a diameter of about 2.0 mm at the opposite end. Because the central section of the pin blank gives as the cutting tool of the lathe is applied, the central section does not have a lineal taper. To obtain a more linear taper, the pin blanks are ground with a grinding wheel attached to a moving bed of the lathe. It is generally necessary to dampen vibrations in the pin blank during the grinding. After the grinding, the end stubs of the pin blanks are removed to leave substantially linearly tapered pins.

The pins are polished with fine emery cloth and heat treated in an oven for approximately two hours at approximately 375° C. The heat treatment oxidizes the surface of the pins to a blueish color. The pins are then coated with a high-temperature graphite release agent available under the trade name of "Graphkote #220 Dry Film Lubricant" from the Joseph Dixon Crucible Co. of Jersey City, N.J.

A cup mold for the collimator block 22 has an interior with a frusto-pyramidal shape. Holes for receiving ends of the tapered pins pass through a base of the cup mold. The holes position the pins in the closely-spaced pattern of the passageways 24 of the collimator block 22 and orient the pins so that the axes of the pins tend to converge to the intended focal point of the collimator. The pins are inserted in the holes in the base of the cup mold, and the cup mold is placed in a closely-fitting mold container to minimize leakage. The cup mold and the mold container are then preheated to approximately 480° C. The mold assembly is then clamped to a steel plate ⅛ in (3.2 mm) thick which is cantilevered from a support table to enable the mold assembly to be vibrated by a mechanical sonic vibrator. The steel plate is vibrated from below with the vibrator while molten lead at approximately 480° C. is poured into the cup mold before the mold assembly has time to cool appreciably. The vibration causes the molten lead to flow into the interstices between the pins so that the resulting lead casting is substantially free of voids. The casting is then allowed to cool and removed from the cup mold. The pins are individually tapped out using a punch and hammer.

It is not intended to limit the present invention to the specific embodiments described above. For example, the X-ray beam can have shapes other than a fan shape. For instance, a shaped X-ray beam can be made up of three or more generally-distinct pencil beams which at the nominal target location are spaced apart in the y-direction a distance corresponding to a y-direction spacing of the directional X-ray detectors and each of which at that location has one of at least two different positions in the z direction. The sensitive volumes in such an embodiment would not fall on a straight line when positioned in a y-z plane. Other shapes of the X-ray beam may be used as well. The X-ray beam may be moved or swept during data collection. The passageways 24 of the collimator assembly 18 may have cross-sectional shapes other than circular. In locating the sensitive volumes on an interfacial surface, the detector assembly may first be moved to an operating base location at which the radiation-intensity signal from the principal X-ray detector at least approximately equals an operating point value corresponding to locating the sensitive volume associated with the principal X-ray detector at a position straddling an interfacial surface, and then subsequently each of the pivotable X-ray detectors may be pivoted to an operating orientation at which the radiation intensity signal from the detector at least approximately equals an operating-point value corresponding to locating the sensitive volume associated with the detector at a position straddling the interfacial surface. It is recognized that these and other changes may be made in the apparatus and process specifically described herein without departing from the scope and teachings of the invention, and it is intended to encompass all other embodiments, alternatives and modifications consistent with the present invention.

We claim:

1. A diagnostic imaging system for constructing an image of an area of an interfacial surface within the body of a subject, the interfacial surface dividing a first region from a second region in the body, contents of the first region differing from contents of the second region in the extent to which unit volumes of such contents scatter penetrating radiation, the system comprising:

(a) radiation source means for generating a shaped beam of penetrating radiation for directing into the body of the subject to illuminate the interfacial surface region;

(b) a scattered-radiation detector assembly including:

(b.1) a detector support frame; and (b.2) a plurality of directional radiation detectors attached to the support frame and spaced apart from the beam of radiation, each directional radiation detector having a directional radiation receptance port and a radiation-intensity signal output and being adapted to produce a radiation-intensity signal at the output which is a measure of the intensity of radiation incident upon the directional radiation receptance port and propagating in a direction admitted by the receptance port, each directional radiation receptance port having a limited field of view, an intersection of a field of view of a directional radiation receptance port of a detector with the beam of radiation defining a sensitive volume;

(c) sensitive-volume positioning means connected to the radiation source means and to the directional radiation detectors and having a position-control signal input for changing at least one of the shape or the orientation or the position of the beam of radiation from the radiation source or the shape or the orientation or the position of the field of view of one of the directional radiation detectors to change controllably the locations of the sensitive volumes associated with the directional radiation detectors in response to sensitive-volume position control signals applied to the position control input;

(d) search control circuit means connected to the radiation-intensity signal output of each of the directional radiation detectors and to the position-control signal input of the sensitive-volume positioning means for directing the sensitive-volume positioning means to move each of the sensitive volume associated with the directional radiation detectors along paths associated with the radiation detectors which intersect the interfacial surface, for monitoring the radiation intensity signal from each of the directional radiation detectors as the associated sensitive volume is moved, and for stopping the sensitive volume associated with each of the directional radiation detectors at an operating position at which one of the radiation-intensity signals from the detector or an average value thereof at least approximately equals an operating point value corresponding to locating the sensitive volume associated with the detector at a position straddling the interfacial surface; and (e) image construction means connected to at least one of the search control circuit means or the directional radiation detectors or the sensitive-volume positioning means for obtaining sensitive-volume location data permitting the relative locations of the operating positions of the sensitive volumes associated with each of the directional radiation detectors to be determined and constructing from the sensitive-volume location data an image of an area of the interfacial surface.

2. The diagnostic imaging system according to claim 1 in which: the detector support frame can be translated along a search path, one of the directional radiation detectors is rigidly attached to the detector support frame and defines a principal directional radiation detector, and each of the remaining directional radiation detectors is pivotably attached to the support frame so that the detector can be pivoted about at least one pivot axis associated with the detector.

3. The diagnostic imaging system according to claim 2 in which the scattered-radiation detector assembly includes at least three directional radiation detectors.

4. The diagnostic imaging system according to claim 3 in which the directional radiation detectors are disposed in a noncollinear array.

5. The diagnostic imaging system according to claim 4 in which the scattered radiation detector assembly includes at least seven directional radiation detectors disposed in a noncollinear array.

6. A diagnostic imaging system for constructing an image of an area of an interfacial surface within the body of a subject, the interfacial surface dividing a first region from a second region in the body, contents of the first region differing from contents of the second region in the extent to which unit volumes of such contents scatter penetrating radiation, the system comprising:
   (a) radiation source means for generating a shaped beam of penetrating radiation for directing into the body of the subject to illuminate the interfacial surface region;
   (b) a scattered-radiation detector assembly including:
      (b.1) detector support frame;
      (b.2) a plurality of directional radiation detectors attached to the support frame and spaced apart from the beam of radiation, at least one of the directional radiation detectors being pivotably attached to the support frame so that the detector can be pivoted about a pivot axis associated with the detector, each directional radiation detector having a directional radiation receptance port and a radiation-intensity signal output and being adapted to produce a radiation-intensity signal at the output which is a measure of the intensity of radiation incident upon the directional radiation receptance port and propagating in a direction admitted by the receptance port, each directional radiation receptance port having a limited field of view, an intersection of a field of view of a directional radiation receptance port of a detector with the beam of radiation defining a sensitive volume; and
      (b.3) at least one detector pivot drive, each detector pivot drive having a pivot-signal input and a drive shaft, the drive shaft being controllably rotatable in response to pivot signals applied to the pivot-signal input, each detector pivot drive being connected to the detector support frame and to a pivotable directional radiation detector so that rotation of the drive shaft of the detector pivot drive causes the directional radiation detector to rotate about the pivot axis associated with the detector;
   (c) search control circuit means connected to the radiation-intensity signal output of each of the pivotable directional radiation detectors and to the pivot-signal input of each of the associated detector pivot drives for selectively directing each of the pivot drives to pivot the corresponding detector to cause the sensitive volume associated with the pivoted radiation detector to intersect the interfacial surface, for monitoring the radiation intensity signal from each of the pivotable directional radiation detectors as the detector is pivoted, and for stopping each of the pivotable directional radiation detectors at an operating orientation at which the radiation-intensity signal from the detector at least approximately equals an operating point value corresponding to locating the sensitive volume associated with the detector at a position straddling the interfacial surface; and
   (d) image construction means connected to at least one of the search control circuit means, the pivotable directional radiation detectors, and the detector pivot drives, for obtaining detector-orientation data specifying the operating orientation of each of the directional radiation detectors and constructing from the detector-orientation data an image of an area of the interfacial surface.

7. The diagnostic imaging system according to claim 6 in which the scattered-radiation detector assembly includes at least three directional radiation detectors, at least two of which are pivotable.

8. The diagnostic imaging system according to claim 7 in which the directional radiation detectors are disposed in a noncollinear array.

9. The diagnostic imaging system according to claim 8 in which the scattered radiation detector assembly includes seven directional radiation detectors disposed in a noncollinear array.

10. The diagnostic imaging system according to claim 8 in which the support frame is movable along a search path, and in which the system further comprises:
   (e) a support frame drive having a drive motion linkage and a drive-signal input, the drive motion linkage being controllably movable in response to drive signals applied to the drive-signal input, the support frame drive being connected to the support frame so that movement of the drive motion linkage causes the support frame to advance along the search path.

11. The diagnostic imaging system according to claim 10 in which the search control circuit means is connected to the drive-signal input of the support frame drive and to a radiation-intensity signal output of a directional radiation detector attached to the support frame which defines a principal radiation detector, and the search control circuit means is adapted (i) to direct the support frame drive to advance the support frame along the search path to cause the sensitive volume associated with the principal radiation detector to intersect the interfacial surface, (ii) to monitor the radiation intensity signal from the principal directional radiation detector as the support frame advances along the search path, and (iii) to stop the support frame at a position on the search path at which the radiation-intensity signal from the principal directional radiation detector at least approximately equals an operating point value corresponding to locating the sensitive volume associated with the principal detector at a position straddling the interfacial surface.

12. The diagnostic imaging system according to claim 6 in which the search control circuit means includes a microcomputer.

13. A process of collecting data which encodes the positions of a plurality of regions on an interfacial surface within the body of a subject for constructing an image of an area of the interfacial surface, the interfacial surface dividing a first region from a second region in the body, contents of the first region differing from contents of the second region in the extent to which unit volumes of such contents scatter penerating radiation, the process comprising the steps of:

(a) directing a shaped beam of penetrating radiation into the body of the subject and through the interfacial surface;

(b) placing a scattered-radiation detector assembly in a pre-search condition, the scattered-radiation detector assembly comprising:

(i) a detector support carriage, the detector support carriage being movable along a search path;

(ii) a principal directional radiation detector attached to the support carriage; and (iii) a plurality of supplementary directional radiation detectors pivotably attached to the support frame; each directional radiation detector having a directional radiation receptance port and a radiation-intensity signal output and being adapted to produce a radiation-intensity signal at the output which is a measure of the intensity of radiation incident upon the directional radiation receptance port, each directional radiation receptance port having a limited field of view, an intersection of a field-of-view of a detector with the beam of radiation defining a sensitive volume, the placing of the detector assembly in a pre-search condition comprising:

(b.1) locating the detector assembly at a pre-search point on the search path so that the sensitive volume associated with the principal directional radiation detector is displaced from the interfacial surface;

(b.2) orienting each supplementary directional radiation detector in a predetermined pre-search orientation so that the sensitive volumes associated with the supplementary radiation detectors are displaced from the interfacial surface;

(c) automatically moving the detector assembly along the search path from the pre-search location to a search termination location while maintaining the orientation of the supplementary detectors substantially fixed at their pre-search orientations so that the sensitive volumes associated with the principal and supplementary detectors approach, traverse, and withdraw from the interfacial surface, which crossing of the interfacial surface by a sensitive volume causing the intensity of radiation scattered into the detector to range between a lower value corresponding to location of the sensitive volume in the first region and a higher value corresponding to location of the sensitive volume in the second region;

(d) monitoring the radiation-intensity singal generated by each directional radiation detector as the detector assembly is moved along the search path and for each detector determining a greater value of the radiation intensity signal together with a location of the detector assembly at which the greater value occurred and a lesser value of the radiation intensity signal together with a location of the detector assembly at which the lesser value occured;

(e) after the greater and the lesser values of the radiation intensity signal from the principal radiation detector have been determined, calculating a trial base location for the detector assembly on the search path substantially equal to a predetermined fraction of the distance between the locations on the search path corresponding to the greater and the lesser values for the radiation intensity signal from the principal directional radiation detector;

(f) after the trial base location of the detector assembly has been calculated, calculating a trial orientation for each supplementary directional radiation detector to cause the sensitive volume associated with the detector to be located, when the detector assembly is positioned at the trial base location, at a position at least approximately equal to a predetermined fraction of the distance on a path between the locations of the sensitive volume for which the radiation intensity signal from the detector attained the greater and the lesser values;

(g) automatically moving the detector assembly to the trial base location;

(h) automatically pivoting each supplementary directional radiation detector to the trial orientation associated with the detector;

(i) calculating an operating point value for each directional radiation detector, the operating point value being calculated from a prespecified function of variables including the greater and the lesser values of the radiation intensity signal associated with the detector, the operating point value so calculated lying between the greater and the lesser values of the radiation intensity signal;

(j) automatically trimming the position of the detector assembly after the detector assembly at least approximately reaches the trial base location by monitoring the radiation-intensity signal from the principal directional radiation detector and automatically moving the detector assembly to cause the radiation-intensity signal from the principal detector or an average value thereof at least approximately to equal the operating point value associated with the principal detector, the detector assembly thereby being placed in an operating base location corresponding to locating the sensitive volume associated with the radiation detector at a position straddling to the interfacial surface;

(k) automatically trimming the orientation of each supplementary directional radiation detector after the detector assembly at least approximately reaches the operating base location by monitoring the radiation-intensity signal from the detector and automatically pivoting the detector to cause the radiation-intensity signal from the detector or an average value thereof at least approximately to equal the operating point value associated with the detector, the detector thereby being oriented in an operating orientation corresponding to locating the sensitive volume associated with the radiation detector at a position straddling the interfacial surface; and (l) transmitting detector-orientation data which encoes the orientation of each supplementary directional radiation detector to a data processing device, thereby collecting data which encodes the positions of the sensitive volumes associated with the directional radiation detectors straddling the interfacial surface.

14. The process according to claim 13 in which the greater value and the lesser value determined for each detector in step (d) are respectively maximum and minimum values.

15. The process according to claim 13 in which the interfacial surface is an interface between a lung cavity and a heart, and in which the sensitive volumes associated with the directional radiation detectors when the detector assembly is in the pre-search condition are located in the lung cavity.

16. A process of collecting data which encodes the positions of a plurality of regions on an interfacial surface in the body of a subject for constructing an image of the interface, the interfacial surface dividing a first region from a second region in the body, contents of the first region differing from contents of the second region in the extent to which unit volumes of such contents scatter penetrating a radiation, the process comprising the steps of:

(a) directing a shaped beam of penetrating radiation into the body of the subject and through the interfacial surface;

(b) orienting each of a plurality of directional radiation detectors in a presearch orientation associated with the detector, each directional radiation detector being pivotably supported outside of the body of the subject, each directional radiation detector having a directional radiation receptance port and a radiation-intensity signal output and being adapted to produce a radiation-intensity signal at the output which is a measure of the intensity of radiation receptance port and propagating in a direction admitted by the receptance port, each directional radiation receptance port having a limited field of view, an intersection of a field-of-view of a directional radiation receptance port of a radiation detector with the beam of radiation defining a sensitive volume;

(c) automatically pivoting each directional radiation detector to cause the sensitive volume associated with the radiation detector to intersect the interfacial surface;

(d) monitoring the radiation intensity signal from each radiation detector as the detector is automatically pivoted and automatically stopping the radiation detector at an orientation at which the radiation-intensity signal or an average value thereof at least approximately equals an operating point value associated with the detector corresponding to locating the sensitive volume associated with the radiation detector at a position straddling the interfacial surface; and (e) transmitting detector-orientation data which encodes the orientation of each directional radiation detector to a data processing device thereby collecting data which encodes the positions of the sensitive volumes associated with the directional radiation detectors straddling the interfacial surface.

17. The process according to claim 16 in which the beam of radiation directed into the subject is fan-shaped.

18. The process according to claim 17 further comprising the steps of:

(f) automatically moving the radiation detectors as a group along a search path beginning at a pre-search point, one of the radiation detectors defining a principal radiation detector, talong a search path beginning at a pre-search point, one of the radiation detectors defining a principal radiation detector, the orientation of the principal radiation detector being maintained in a fixed direction as the radiation detectors are moved, the movement of the radiation detectors along the search path causing the sensitive volume associated with the principal radiation detector to intersect the interfacial surface so that the intensity of the radiation scattered into the principal radiation detector from the associated sensitive volume changes; and (g) monitoring the radiation-intensity signal generated by the principal radiation detector as the detectors are moved along the search path and automatically stopping the detectors when the radiation-intensity signal from the principal radiation detector or an average value thereof at least approximately equals an operating-point value corresponding to locating the principal sensitive volume at a position straddling the interfacial surface.

19. A process of collecting data which encodes the positions of a plurality of regions on an interfacial surface in the body of a subject for constructing an image of an area of the interfacial surface, the process comprising the steps of:

(a) directing a shaped beam of penetrating radiation into the body of the subject and through the interfacial surface;

(b) placing a scattered-radiation detector assembly in a pre-search condition, the scattered-radiation detector assembly comprising:

(i) a detector support frame, the detector support frame being movable along a search path;

(ii) a principal directional radiation detector attached to the support frame; and (iii) a plurality of supplementary directional radiation detectors pivotably attached to the support frame; each directional radiation detector having a radiation receptance port and a radiation-intensity signal output and being adapted to produce a radiation-intensity signal at the output which is a measure of the intensity of the radiation incident upon the directional radiation receptance port and propagating in a direction admitted by the receptance port, each radiation receptance port having a limited field of view, an intersection of a field-of-view of a directional radiation receptance port of a radiation detector with the beam of radiation defining a sensitive volume, the placing of the detector assembly in a pre-search condition comprising:

(b.1) locating the detector assembly at a pre-search point on the search path so that the sensitive volume associated with the principal directional radiation detector is displaced from the interfacial surface; and (b.2) orienting each supplementary directional radia detector in a predetermined pre-search orientation;

(c) automatically moving the detector assembly along the search path while maintaining the orientation of the supplementary detectors substantially fixed at their pre-search orientations so that the principal sensitive volume approaches and intersects the interfacial surface, the intersection of the principal sensitive volume with the interfacial surface causing a change in the intensity of radiation scattered into the detector from the sensitive volume;

(d) monitoring the radiation-intensity signal generated by the principal radiation detector as the detector assembly is moved along the search path and automatically stopping the detector assembly when the radiation-intensity signal from the principal radiation detector or an average value thereof at least approximately equal an operating-point value corresponding to locating the principal sensitive volume at a position straddling the interfacial surface;

(e) automatically pivoting each supplementary directional radiation detector after the radiation intensity signal from the principal radiation detector approximately equals the operating-point value to cause the sensitive volume associated with the supplementary radiation detector to intersect the interfacial surface;

(f) monitoring the radiation intensity signal from each supplementary radiation detector as the detector is pivoted and automatically stopping the supplementary radiation detector at an orientation at which the radiation-intensity signal or an average value thereof at least approximately equals an operating-point value corresponding to locating the sensitive volume associated with the detector at a position straddling the interfacial surface; and (g) transmitting detector-orientation data which encodes the orientation of each supplementary directional radiation detector to a data processing device, thereby collecting data which encodes the positions of the sensitive volumes associated with the directional radiation detectors straddling the interfacial surface.

20. A process according to claim 19 in which the principal sensitive volume is located outside of the body of the subject when the detector assembly is positioned at the pre-search location.

* * * * *

UNITED STATES PATENT AND TRADEMARK OFFICE
CERTIFICATE OF CORRECTION

PATENT NO. : 4,495,636
DATED : January 22, 1985
INVENTOR(S) : Alan M. Jacobs, et al It is certified that error appears in the above-identified patent and that said Letters Patent are hereby corrected as shown below:

Claim 13, column 20, line 55 "encoes" should be --encodes--.

Claim 18, column 21, line 60, 61 and 62, delete "talong a search path beginning at a pre-search point, one of the radiation detectors defining a principal radiation detector;".

Signed and Sealed this

Seventeenth Day of September 1985

[SEAL]

Attest:

Attesting Officer

DONALD J. QUIGG

Commissioner of Patents and Trademarks—Designate